(12) United States Patent
Sourdille et al.

(10) Patent No.: US 6,179,870 B1
(45) Date of Patent: Jan. 30, 2001

(54) FLEXIBLE INTRAOCULAR IMPLANT FORMED IN ONE PIECE

(75) Inventors: Philippe Sourdille, Nantes; Angel Ortuno, Choisy, both of (FR)

(73) Assignee: Corneal Laboratoires, Paris (FR)

( * ) Notice: Under 35 U.S.C. 154(b), the term of this patent shall be extended for 0 days.

(21) Appl. No.: 09/180,203

(22) PCT Filed: Apr. 30, 1997

(86) PCT No.: PCT/FR97/00772

§ 371 Date: Nov. 2, 1998

§ 102(e) Date: Nov. 2, 1998

(87) PCT Pub. No.: WO97/41805

PCT Pub. Date: Nov. 13, 1997

(30) Foreign Application Priority Data

May 3, 1996 (FR) .................................................. 96 05585

(51) Int. Cl.[7] ....................................................... A61F 2/16
(52) U.S. Cl. ........................................... 623/6.39; 623/6.49
(58) Field of Search ..................................... 623/6.39, 6.4, 623/6.43, 6.49, 6.51–6.55, 6.38, 6, 6.42, 6.46

(56) References Cited

U.S. PATENT DOCUMENTS

| 4,787,904 | 11/1988 | Severin et al. . |
| 4,990,159 | * 2/1991 | Kraff ................................... 623/6.49 |
| 5,133,749 | 7/1992 | Nordan . |

FOREIGN PATENT DOCUMENTS

| 0 579 528 | 1/1994 | (EP) . |
| 0 766 952 | 4/1997 | (EP) . |
| 2 701 390 | 8/1994 | (FR) . |
| 2 144 041 | 2/1985 | (GB) . |
| 2 180 160 | 3/1987 | (GB) . |
| WO 94 28825 | 12/1994 | (WO) . |

* cited by examiner

Primary Examiner—David H. Willse
(74) Attorney, Agent, or Firm—Wolf, Greenfield & Sacks, P.C.

(57) ABSTRACT

The invention concerns an intraocular implant comprising a substantially circular optical part (10) and two curved haptic loops (12, 14) each with a first connecting end (12a, 14a) at the periphery of the optical part and a free second end (12b, 14b) intended to come to rest on the internal wall of the eye, characterized in that the optical part (10) and the haptic loops (12, 14) are made of the same flexible material, the elastic modulus thereof being in a range between 0.25 MPa and 1 MPa, and in that the width of each loop decreases from its connecting end to its free end such that the ratio between the bending moment variation and the inertia moment variation at two separate points (P1, P2) of the loop is substantially constant.

8 Claims, 3 Drawing Sheets

FLEXIBLE INTRAOCULAR IMPLANT FORMED IN ONE PIECE

The present invention has for its object a flexible intraocular implant formed in one piece and, particularly but not exclusively, an implant of this type intended to be placed in position in the capsular sac after ablation of the lens.

Intraocular implants may be divided into two large categories depending on the material with which they are made. So-called flexible intraocular implants and so-called rigid intraocular implants are distinguished. The former are made with materials of the silicone gel or pHEMA type, the latter generally being made from PMMA.

Rigid implants made of PMMA have been developed and manufactured for numerous years and their shape is perfectly defined. In particular, it is the case for the shape of the haptic loops, the function of these loops being to come to rest on the periphery of the capsular sac or on the internal wall of the eye in order elastically to maintain the optical portion of the implant opposite the pupil of the patient who has been implanted.

The tendency in eye surgery and, more precisely, in the positioning of intraocular implants in the eye, is to reduce very substantially the dimension of the incision which must be made in the cornea to position the intraocular implant. It must be added that, the implant is most often placed in position in the capsular sac after ablation of the lens, the techniques of ablation of the lens, particularly phako-emulsification, may be carried out by making only an incision of reduced dimensions, typically of the order of 3 to 4 mm. It was therefore interesting to have available intraocular implants capable of being placed in position in the eye through such an incision. However, it will be understood that the dimensions of the optical portion of the implant, i.e. its diameter, must be sufficient for this optical portion to perform its role of correction, even when the pupil is dilated to a maximum and despite a slight off-centering of the optical portion. It is therefore necessary that the optical portion presents a sufficient diameter, typically of the order of 5 to 6 mm.

Taking all these constraints into account, it will therefore be understood that only the use of a flexible material allowing the optical portion to be bent makes it possible to satisfy the double condition of passing through an incision in the cornea of reduced dimensions and of guaranteeing a sufficient diameter of the optical portion to allow optical correction, whatever the situation.

Consequently, a large number of so-called flexible intraocular implants have been developed to satisfy these two conditions. However, although the so-called flexible materials contribute an interesting solution to the problem of producing the optical portion, it is not so concerning the production of the haptic portion. In fact, the great flexibility of these materials means that the direct transposition of the haptics of the implants made of hard material cannot give satisfaction in the case of the flexible materials.

Taking this situation into account, two great types of solution have been proposed: on the one hand, it has been proposed to make implants in which the optical portion is flexible and the haptic portion is rigid, typically made of PMMA. These techniques are described in particular in Patent Application PCT/FR95/01344. This solution makes it possible, on the one hand, to benefit from pliable, flexible optics and, on the other hand, to use haptic loops made of PMMA of which the geometrical definition is perfectly mastered. It has also been proposed to make the haptic portion for the flexible implants, not via two loops in C or J form disposed diametrally with respect to the optics, but by providing two much more solid haptic portions terminating in arc-of-circle edges of sufficient length to ensure a sufficient contact between the periphery of the capsular sac and the haptic portion. Such flexible implants are described in particular in European Patent Application No. 93401744.3.

Nonetheless, it has already been proposed to make flexible implants in one piece, with a haptic portion constituted by two short loops of relatively conventional type. However, these implants are unsatisfactory insofar as, due to the very great flexibility of this material which presents a modulus of elasticity typically less than 0.2 MPa, the haptic loop, under the effect of the stresses resulting from its being positioned in the capsular sac, bends locally in the region of the connection of the loop to the periphery of the optical portion. This results in that the effective zone of contact between the haptic loops and the periphery of the capsular sac is reduced, which does not ensure perfect maintenance in place of the optical portion and which risks, especially, causing a deformation of the capsular sac with the damaging consequences that this brings about, or even a perforation of this capsular sac under the effect of the concentration of the pressure stresses.

This is shown in FIG. 6, the optical portion being referenced 2, the haptic loops 4 and the periphery of the capsular sac 6.

One object of the present invention is to provide a flexible one-piece intraocular implant presenting a haptic portion constituted by loops but which comprises a haptic portion having improved properties of maintenance and flexibility to obtain results substantially equivalent to those which are obtained with haptic loops made of PMMA.

To attain this object, the intraocular implant which comprises a substantially circular optical portion and two curved haptic loops each with a first connecting end at the periphery of the optical portion and a free end intended to come to rest on the internal wall of the eye, is characterized in that the optical portion and the haptic loops are made of the same flexible material of which the modulus of elasticity is included between 0.25 MPa and 1 MPa, and in that the width in the optical plane of each loop decreases from its connecting end to its free end such that the varation of the ratio between the variation of the bending moment applied to the loop and the inertia moment variation is substantially constant between two separate points of the loop over the whole length of the loop.

Thanks to this specific definition of the geometry of the loop, a distributed bending of the loop is obtained which thus enables it to adapt itself by bending to the different internal diameters of the capsular sac, avoiding a localized bending of the loop at the level of its connection to the optical portion and thus producing a considerable length of contact between the loop and the internal wall of the capsular sac or of the eye depending on the modes of implantation.

According to a preferred embodiment, each haptic loop further comprises a complementary arm separate from the loop proper and of which a first end is connected to the periphery of the optical portion near the connecting end of the loop and of which the other end is connected to the loop near its free end, the section of said additional arm being smaller than that of the loop, said arm being disposed on the concave side of the loop.

Thanks to the presence of a complementary arm associated with each haptic loop proper, not only the bending properties of the loops according to the definition given hereinabove are conserved, but, in addition, the inertia moment of each haptic loop is increased with respect to the risks of torsion of the loop with respect to its neutral axis. This thus makes it possible to avoid a relative movement of rotation of the optical portion with respect to the two loops, this movement of rotation risking producing a displacement of the optical portion such that the plane of the optical portion is no longer perpendicular to the optical axis of the eye.

Other characteristics and advantages of the invention will appear more readily from reading the following description of several embodiments of the invention given by way of non-limiting examples. The description refers to the accompanying Figures in which:

FIG. 1b is a side view of the intraocular implant of FIG. 1a.

FIG. 2b is a side view of the intraocular implant of FIG. 2a.

Figure 1A:
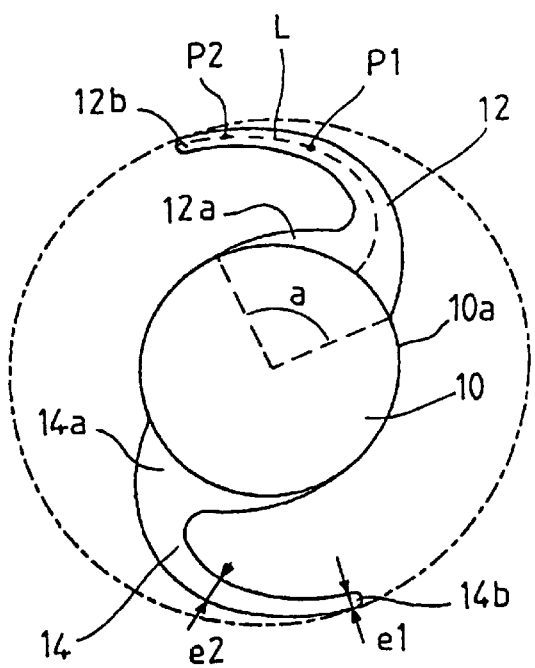
FIG. 1a is a front view of a first embodiment of the flexible intraocular implant.
Figure 1B:
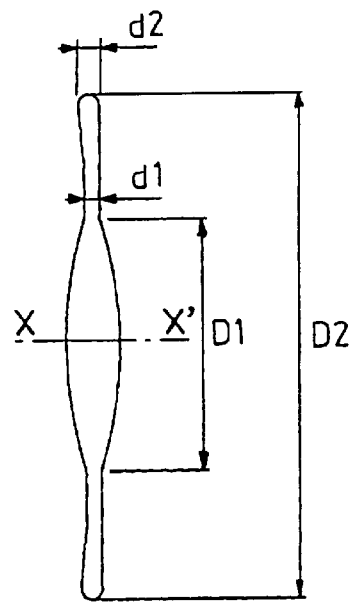

Referring firstly to FIGS. 1a and 1b, and to FIG. 3, a first embodiment of the one-piece, flexible intraocular implant will be described. As shown in FIG. 1a, the intraocular implant is constituted by an optical portion 10 of substantially circular shape, limited by an anterior diopter and a posterior diopter and by a haptic portion constituted by two loops 12 and 14, these two loops being identical or substantially identical and connected to the periphery 10a of the optical portion at two substantially diametrally opposite points. These loops in C form present a curvature which varies regularly without presenting singular points.

According to an essential characteristic of the invention, the implant is in one-piece, i.e. the optical portion 10 and the haptic loops 12 and 14 constitute only one piece, this piece being a pHEMA, for example hydrogel. The modulus of elasticity of the composition of pHEMA used is included between 0.25 MPa and 1 MPa. According to the particular embodiment described, the modulus of elasticity is preferably equal to 0.6 MPa. It is therefore seen that, to make the one-piece flexible implant, a type of pHEMA presenting a modulus of elasticity greater than the pHEMA conventionally used, is employed. However, by limiting the modulus of elasticity to 1 MPa, there is still the possibility of bending the optics easily and of maintaining the optics bent with a force of hold compatible with the surgical operation.

In addition, as is seen, each loop 12 comprises a zone, a connecting end 12a which presents a considerable width with respect to the running part of the loop and which is therefore connected at an angle at the center a of the optical portion which is relatively large, for example of the order of 80 degrees and more generally included between 60 and 90 degrees, and a second free end 12b intended to come to rest on the internal wall of the capsular sac or of the eye depending on the mode of implantation retained.

According to an essential characteristic of the invention, if the neutral axis of the loop is considered and if two points P1 and P2 of this neutral axis are considered, the geometry of the running part of the loop is made in such a manner that the ratio of the variation of the bending moment present at points P1 and P2, due to the effort applied to the loop when it is placed in position in the eye, and of the variation of the inertia moment at these two points P2 and P1, is substantially constant.

To that end, and if a force exerted on the end of the loop is considered, then the bending moment will increase as one approaches the optics in substantially linear fashion. It is therefore a question of varying the inertia moment in the same way. The inertia moment will be expressed in the following manner: $I_2=I_0+1\times\Delta I$.

$I_0$ is the inertia moment at the end of loop, 1 being the distance (in mm) which separates the end of the loop at the point in question, this distance being taken on said neutral axis.

$\Delta I$ is the coefficient of variation of the inertia moment. This variation of inertia moment is expressed in mm$^4$. $\Delta I$ is preferably included between $5.10^{-4}$ and $15.10^{-4}$.

Thanks to this arrangement, a curvature is thus obtained by regular bending of the loop when the implant is placed in position within the capsular sac. For example, in FIG. 1a–1b, the diameter D1 of the optical portion is 6 mm, while the external diameter D2 of the haptic portion at rest is equal to 12 mm.

Figure 3:
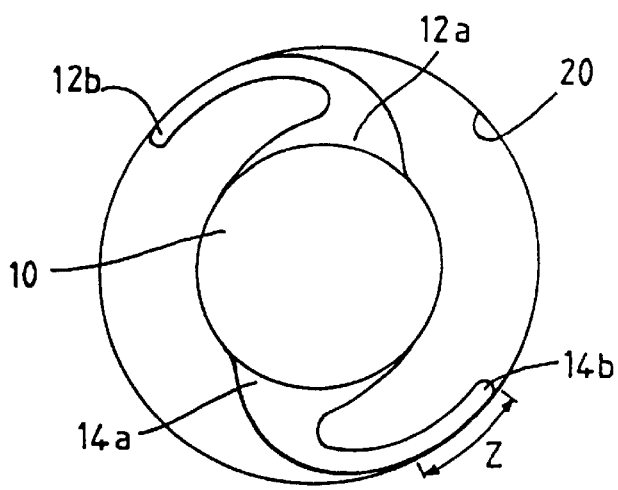
FIG. 3 is a view of the intraocular implant of FIG. 1a placed in position in the capsular sac.

FIG. 3 shows the deformation of the loop when the implant is positioned in a capsular sac 20 of internal diameter 11 mm. It is seen that the bending of each loop, instead of being concentrated in the zones of connection 12a to 14a, is developed over the whole of the length of the loop 12–14, which makes it possible to have a considerable zone of contact Z between the part of the loop close to its free end 12b14b with the internal wall of the capsular sac.

It will be understood that this relatively large length of contact avoids a localized deformation of the capsular sac, due to the fact that the punctual pressure applied is distributed over the whole of the zone Z and not in a limited number of points, as in the case of the implants of the state of the art. In addition, this arrangement makes it possible to avoid the risks of perforation of a capsular sac due to a considerable localized pressure. Finally, as this zone Z presents a relative long length, there is good abutment of each loop on the internal wall of the capsular sac and therefore a good hold of the optical portion in place.

In order to obtain this constancy or substantial constancy of the ratio of the variation of the bending moment applied to the loop on the variation of the inertia moment, the loop preferably has in the optical plane, a width e which decreases from its connecting end 14a towards its free end 14b. FIG. 1a shows a width e2 close to the connecting zone equal to 0.55 mm and a width e1 at its end 14b which is 0.35 mm. As shown in FIG. 1b, on the other hand, if the thickness d of each loop is considered, i.e. its dimension in the direction of the optical axis XX', this thickness d increases from the periphery of the optical portion towards the free end. In zone d1, this thickness is typically 0.35 mm, while at the free end 12b, this thickness d2 is 0.45 mm. To that end, the inertia moment varies as a function of the distance which separates the end of the loop with respect to the point in question on the neutral axis with a coefficient included between $5.10^{-4}$ and $15.10^{-4}$. The moment is expressed in mm$^4$ and the distance in mm.

Referring now to FIGS. 2a, 2b and 4a, 4b, a second embodiment of the one-piece, flexible, intraocular implant according to the invention will be described. In this embodiment, each haptic loop 12, 14 and which has, in the running part, the same dimensions as the loops of the embodiments of FIG. 1a, is completed by an additional arm respectively referenced 22, 24. Each arm 22, 24 also comprises a connecting end 22a at the periphery of the optical portion and a free end 22b at the free end 12b, 14b of the associated loop. The arm 22 or 24 has a substantially constant width e' except, of course, in its connecting end part 22b, 24b where this thickness is greater to ensure continuity with the loop 12, the width e' is typically equal to 0.25 mm. In this way, the assembly constituted by the loop 12 and the arm 22 or loop 14 and the arm 24 defines between these two elements a recess respectively referenced 26 and 28.

This improved embodiment presents all the advantages of the embodiment of FIG. 1a, concerning the bending qualities of the loops 12 and 14 proper but, in addition, the mechanical coupling of the arms 22 and 24 with the loops 12 and 14 makes it possible to avoid the risks of rotation of the optical portion 10, by reason of the risks of torsion of the loops 12 and 14, due to their being constituted by a relatively flexible material. In fact, the additional arms 22 and 24 being directly connected to another zone of the periphery of the optical portion and to the free end of each loop, this movement of torsion is avoided or, at least, the risks thereof are considerably reduced.

Figure 2A:
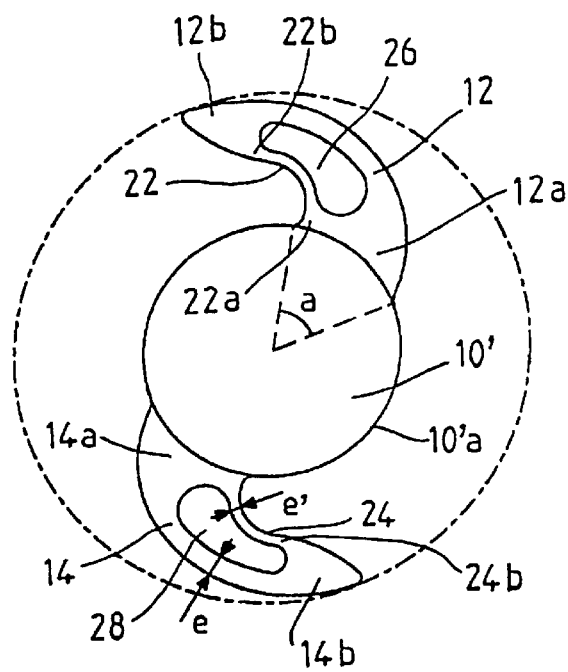
FIG. 2a is a front view of a second embodiment of the flexible intraocular implant.
Figure 2B:
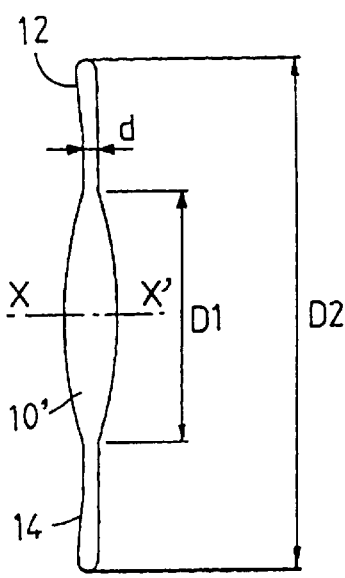
Figure 4A:
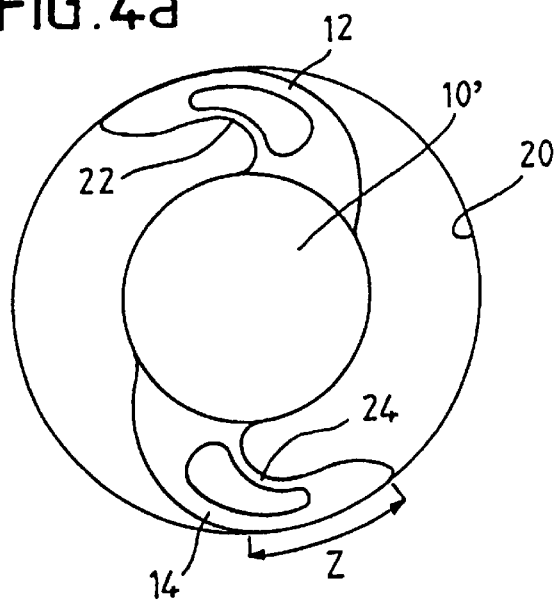
FIGS. 4a and 4b show an intraocular implant of the type shown in FIG. 2a placed in position in capsular sacs of different diameter.
Figure 4B:
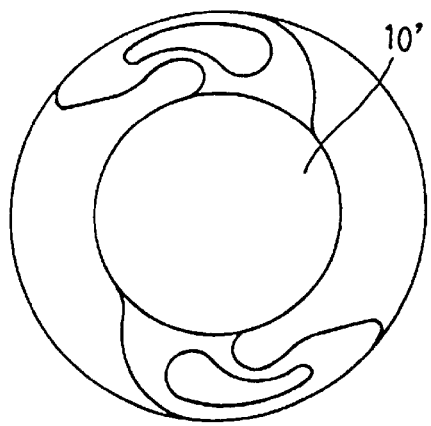
Figure 6:
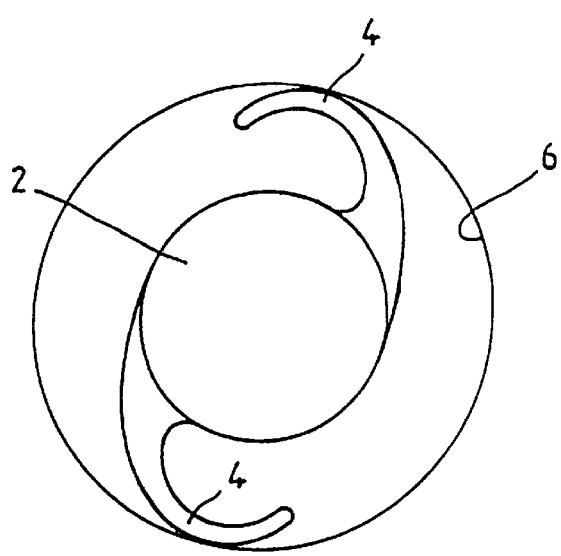
FIG. 6, already described, shows a flexible implant of the prior art placed in position in the capsular sac.

FIGS. 4a and 4b show the positioning of the intraocular implant 10' of FIG. 2a in a capsular sac 20 of which the internal diameter is respectively equal to 11 mm for FIG. 4a and 10 mm for FIG. 4b. These Figures show in particular the deformation by bending of the loops 12 and 14 and of the arms 22 and 24. It is observed that there is still a relatively large zone Z of contact between the haptic loops and the periphery 20 of the capsular sac, which, of course, presents the same advantages as those which were described in connection with FIG. 3.

Figure 5A:
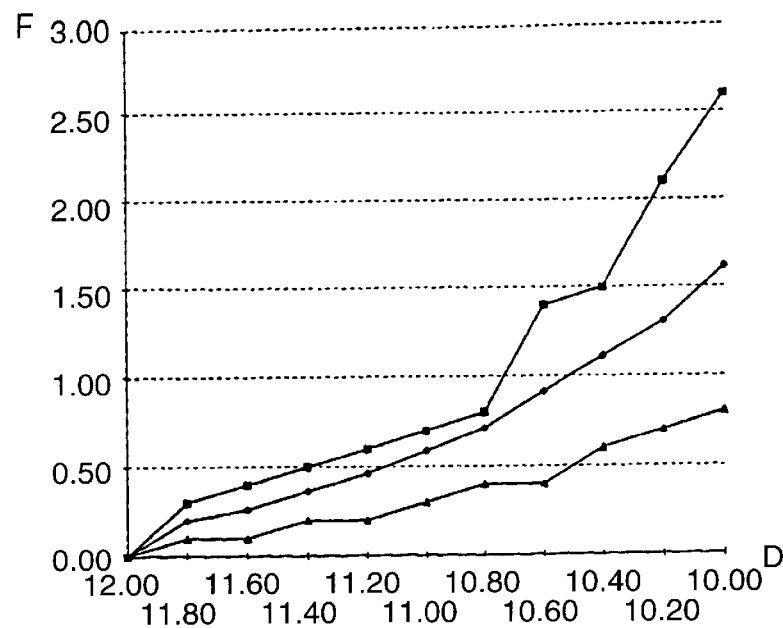
FIG. 5a to 5c are curves showing the force of compression as a function of the final diameter of the implant after it has been placed in position in the capsular sac.
Figure 5B:
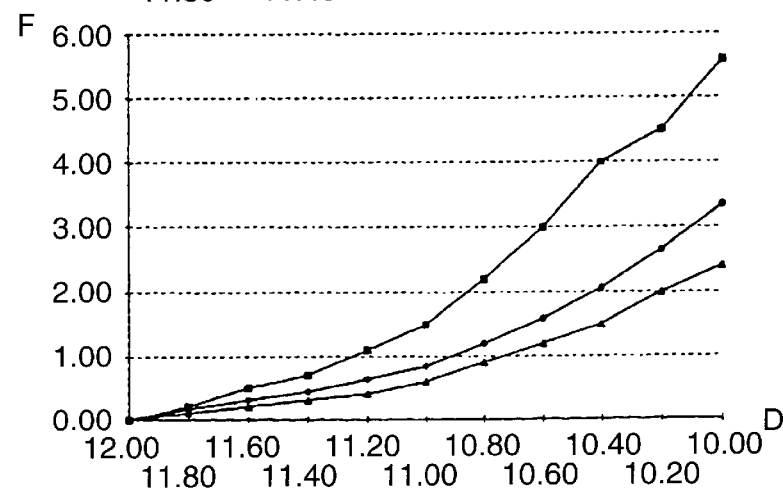
Figure 5C:
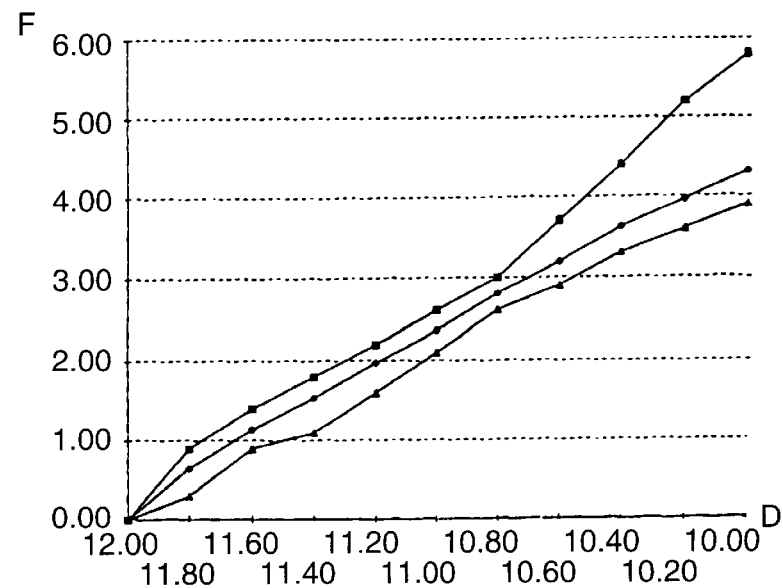

FIGS. 5a to 5c show the tests made respectively on a one-piece flexible implant of the prior art (5a), and on the implants of FIG. 1a (5b) and FIG. 2a (5c). Each diagram represents the force of compression F as a function of the external diameter D of the haptic portion, the diameter D at rest being equal to 12 mm.

In the case of FIG. 5a, it is seen that the force of compression is much reduced while, in the case of FIGS. 5b and 5c, this force of compression is much higher for the same diameter, which ensures a much better holding in place of the optical portion in the eye.

What is claimed is:

1. Intraocular implant comprising a substantially circular optical portion and two curved haptic loops each with a first connecting end at a periphery of the optical portion and a free second end intended to come to rest on an internal wall of an eye, said optical portion and said haptic loops being made of a same flexible material having a modulus of elasticity between 0.25 MPa and 1 MPa, a width of each loop decreasing from its connecting end to its free end such that a ratio between a variation of a bending moment and a variation of an inertia moment is substantially constant between two separate points of the loop.

2. The intraocular implant according to claim 1 wherein the inertia moment variation divided by a distance which separates the second end of the loop from a point in question on a neutral axis of the loop is between $5.10^{-4}$ mm$^3$ and $15.10^{-4}$ mm$^3$, the inertia moment being expressed in mm$^4$ and the distance in mm.

3. The intraocular implant according to claim 1 wherein each haptic loop further comprises a complementary arm separated from the loop proper and of which a first end is connected to the periphery of the optical portion near the connecting end of the loop and of which a second end is connected to the loop near its free end, the cross section of said complementary arm being smaller than that of the loop, said arm being disposed on a concave side of the loop.

4. The intraocular implant according to claim 3, wherein a thickness of each loop in a direction of an optical axis increases from the connecting end towards the free end.

5. The intraocular implant according to claim 1 wherein the connecting end of each loop extends on the periphery of the optical portion over a length corresponding to an angle $\alpha$ at a center of the optical portion included between 60 and 90 degrees.

6. The intraocular implant according to claim 1, wherein said optical portion has a diameter greater than about 5 mm prior to implantation in an eye.

7. The intraocular implant according to claim 1, wherein the optical portion may be bent with a holding force compatible with a surgical instrument prior to implantation.

8. An intraocular implant comprising:
a substantially circular optical portion having a diameter greater than about 5 mm and two curved haptic loops each with a first connecting end at a periphery of the optical portion and a free second end intended to come to rest on an internal wall of an eye, said optical portion and said haptic loops being made of a same flexible material having a modulus of elasticity between 0.25 MPa and 1 MPa, wherein the optical portion may be bent with a holding force compatible with a surgical instrument, a width of each loop decreasing from its connecting end to its free end such that a ratio between a variation of a bending moment and a variation of an inertia moment is substantially constant between two separate points of the loop.

* * * * *